(12) United States Patent
Pittelkow et al.

(10) Patent No.: US 7,687,645 B2
(45) Date of Patent: Mar. 30, 2010

(54) INTERMEDIATES FOR THE PREPARATION OF CITALOPRAM AND ESCITALOPRAM

(75) Inventors: Thomas Pittelkow, Svinninge (DK); Andrea Castellin, Mestrino (IT); Federico Sbrogiò, Montecchio Maggiore (IT); Poul D. Nielsen, Vig (DK); Jacobo Zanon, Venezia (IT); Steen Sogaard, Padova (IT); Rikke E. Humble, Kobenhavn NV (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 608 days.

(21) Appl. No.: 10/550,419

(22) PCT Filed: Mar. 17, 2004

(86) PCT No.: PCT/DK2004/000177

§ 371 (c)(1),
(2), (4) Date: May 30, 2007

(87) PCT Pub. No.: WO2004/083197

PCT Pub. Date: Sep. 30, 2004

(65) Prior Publication Data

US 2008/0058536 A1 Mar. 6, 2008

Related U.S. Application Data

(60) Provisional application No. 60/456,415, filed on Mar. 21, 2003.

(30) Foreign Application Priority Data

Mar. 21, 2003 (DK) ............... 2003 00440

(51) Int. Cl.
 *C07D 307/93* (2006.01)
(52) U.S. Cl. ................................ 549/302
(58) Field of Classification Search ............ 549/263, 549/302
See application file for complete search history.

(56) References Cited

U.S. PATENT DOCUMENTS

| 3,607,884 A | 9/1971 | Forney |
| 4,650,884 A | 3/1987 | Bogeso |
| 4,943,590 A | 7/1990 | Boegesoe et al. |
| 6,403,813 B1 * | 6/2002 | Petersen et al. ............. 549/305 |
| 6,458,973 B1 | 10/2002 | Dall'Asta et al. |

FOREIGN PATENT DOCUMENTS

| DE | 2630927 | | 1/1978 |
| EP | 1118614 | | 7/2001 |
| GB | 1578989 | | 11/1980 |
| JP | 62185070 A2 | | 8/1987 |
| WO | WO 98/19511 | | 5/1998 |
| WO | WO 98/19513 | | 5/1998 |
| WO | WO 99/16743 | | 4/1999 |
| WO | WO 0039112 | * | 6/2000 |
| WO | WO 00/39112 | | 7/2000 |
| WO | WO 00/44738 | | 8/2000 |
| WO | WO 01/32642 | | 5/2001 |

OTHER PUBLICATIONS

Hyttel, *Prog. Neuro-Psychopharmacol & Biol Psychiat*, 1982, (6):277-295.
Gravem, *Acta Psychiatr Scand*, 1987, (75):478-486.
Tirouflet, *Bull Soc Sci Bretagne*, 1951, (26):35-43.
Levy and Stephen, *J Chem Soc*, 1931, 867-870.
Forney, *J Org Chem*, 1970, (35):1695-1696.
Anzalone and Hirsch, *J Org Chem*, 1985, (50):2128-2133.
Forney, *J Org Chem*, 1971 (36):689-693.
Sugimori and Yashima, *Chemistry Letters*, 1980, 483-486.
*J Chem Soc*, 77; 1900; 278.

* cited by examiner

*Primary Examiner*—D. Margaret Seaman
*Assistant Examiner*—Nizal S Chandrakumar
(74) *Attorney, Agent, or Firm*—Darby & Darby P.C.

(57) ABSTRACT

Methods for manufacture of 5-alkoxycarbonylphthtalides are disclosed. The 5-alkoxycarbonylphthtalides are useful in syntheses of the well-known antidepresssants citalopram and escitalopram.

16 Claims, No Drawings

INTERMEDIATES FOR THE PREPARATION OF CITALOPRAM AND ESCITALOPRAM

This application is a § 371 national stage of International Application No. PCT/DK2004/000177, filed Mar. 17, 2004, which was published in English as International Publication No. WO 2004/083197, and claims the benefit of U.S. Provisional Application No. 60/456,415, filed Mar. 21, 2003 and Danish Patent Application No. PA 200300440, filed Mar. 21, 2003.

The present invention relates to a process for the preparation of intermediates used in the manufacture of the antidepressant drug citalopram, 1-[3-(dimethylamino)propyl]-1-(4-fluorophenyl)-1,3-dihydro-5-isobenzofurancarbonitrile.

BACKGROUND OF THE INVENTION

Citalopram is a well-known antidepressant drug that has now been on the market for some years. Citalopram has the following structure (I):

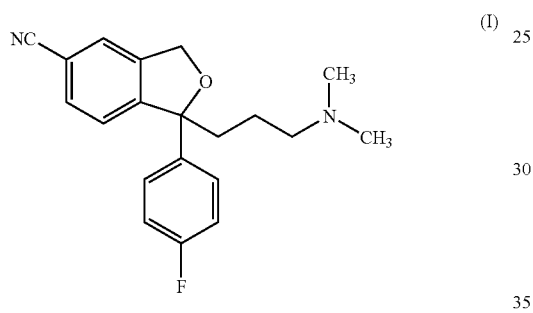

It is a selective, centrally active serotonin (5-hydroxytryptamine; 5-HT) reuptake inhibitor, accordingly having antidepressant activities. The antidepressant activity of the compound has been reported in several publications, e.g. J. Hyttel, *Prog. Neuro-Psychopharmacol. & Biol. Psychiat.*, 1982, 6, 277-295 and A. Gravem, *Acta Psychiatr. Scand.*, 1987, 75, 478-486.

Citalopram may be prepared by the process described in U.S. Pat. No. 4,650,884, according to which 5-cyanophthalide is subjected to two successive Grignard reactions, i.e. with 4-fluorophenyl magnesium halogenide and N,N-dimethylaminopropyl magnesium halogenide, respectively, and the resulting compound of the Formula (II) is subjected to a ring closure reaction by dehydration with strong sulfuric acid.

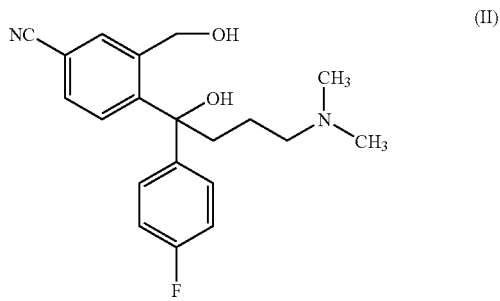

Enantiomers of citalopram may be prepared by the method described in U.S. Pat. No. 4,943,590, i.e. by separating the enantiomers of the intermediate of Formula (II) and performing enantioselective ring closure in order to obtain the desired enantiomer.

Thus, 5-cyanophthalide is an important intermediate for the manufacture of citalopram and escitalopram and it is important to produce this material in an adequate quality, by a convenient process and in a cost-effective way.

A method for the preparation of 5-cyanophthalide has previously been described in Tirouflet, Bull. Soc. Sci. Bretagne, 26, 1951, 35 and in Levy and Stephen, J. Chem. Soc., 1931, 867.

WO 00/39112 describes a method for the preparation of 5-cyanophthalide from 5-carboxyphthalide in which 5-carboxyphthalide is treated with an alcohol R—OH in the presence of an acid to produce an ester corresponding to the compound of Formula (II), i.e. $R^3$ corresponding to R; R is disclosed as $C_{1-6}$-alkyl or phenyl.

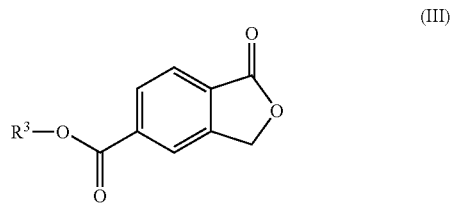

In WO 00/39112 $C_{1-6}$ alkyl is defined as referring to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl-1-ethyl and 2-methyl-1-propyl. In WO 00/39112 is also disclosed the preparation of 5-ethoxycarbonylphthalid by suspension of 5-carboxyphthalide in ethanol, addition of $POCl_3$ followed by heating to reflux temperature for 5 hours. The precipitate was filtered of and washed with ethanol. Similarly, 5-ethoxycarbonylphthalid was prepared by suspension of 5-chlorocarbonylphthalid in ethanol, heating of the mixture to reflux for 15 minutes, followed by cooling, filtration and washing the collected precipitate with ethanol.

Further, WO 00/39112 discloses the conversion of the compound of Formula (III) to an amide having the Formula (IV) by amidation with ammonia or a $C_{1-6}$-alkylamine, e.g., t-butyl amine; R is H or $C_{1-6}$ alkyl.

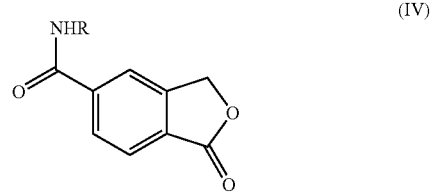

Finally, in WO 00/39112 the amide of Formula (IV) is reacted with a dehydrating agent, e.g. $SOCl_2$, thereby obtaining 5-cyanophthalide having the Formula (V).

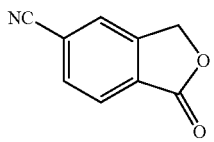

(V)

JP 62185070 A2 describes use of phthalimides for treatment of angina pectoris.

A further method for the preparation of 5-cyanophthalide from 5-carboxyphthalide is described in WO 00/044738. Reference is also made to WO 98/19513 and WO 98/19511 describing methods for the preparation of citalopram.

The preparation of 5-carboxyphthalide of Formula (VI) from terephthalic acid of Formula (VII) is described in, e.g., U.S. Pat. Nos. 6,403,813, 6,458,973, 3,607,884 and by Forney, L. S, J. Org. Chem. 1970, 35, p. 1695-1696.

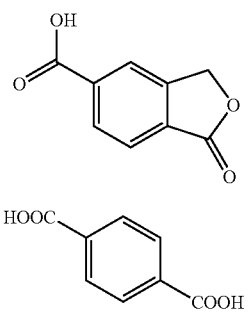

(VI)

(VII)

Accordingly, U.S. Pat. No. 3,607,884 discloses a method of producing 5-carboxyphthalide by reaction of terephthalic acid with formaldehyde and $SO_3$, followed by addition of water. U.S. Pat. No. 3,607,884 also discloses a reaction of formaldehyde with terephthalic acid and $SO_3$ which is cooled down and poured into alcohol (e.g. methanol or ethanol); it is stated that thereby the corresponding ester of 5-carboxyphthalide is produced and that this ester subsequently can be converted to 5-carboxyphthalide. Forney, L. S, J. Org. Chem. 1970, 35, p. 1695-1696 and U.S. Pat. No. 3,607,884 further discloses the preparation of 5-methoxycarbonylphtalide and 5-ethoxycarbonylphtalide by esterification of 5-carboxyphthalide. Another method is described by Anzalone L. and Hirsch J. A, J. Org. Chem. 1985, 50, 2128-2133 in which an ester substituted phthalide is prepared from diethyl 2-methylterepthalate.

Forney, L. S, J. Org. Chem. 1970, 35, p. 1695-1696 discloses a reaction of terephthalic acid (Formula VII), trioxane, and sulfuric acid by heating to 150° C. for 2 hours in a sealed glass tube; the tube was chilled and opened and the content poured into methanol, concentrated, poured into water, and extracted into dichloromethane. The yield of this reaction is disclosed as 83.2% dimethyl terephthalate and 1.1% 5-methoxycarbonylphtalide.

Furthermore, a reaction of oleum, terephthalic acid and formaldehyde is also disclosed in Forney, L. S, J. Org. Chem. 1971, 36, p. 689-693. WO9916743 discloses compounds with alkoxycarbonyl groups, among which are compounds corresponding to formula III.

Sugimori, A. and Yashima, T, Chemistry Letters, 1980, 483-486, describes gamma-radiation of aromatic carboxylic esters in alcohol solutions, exemplified by radiation of dimethyl terephthalate. In this connection is disclosed a formula corresponding to the compound of formula (III) wherein $R^3$ is methyl. Similarly, Anzalone L. and Hirsch J. A., J. Org. Chem 1985, 2128-2133 describes the preparation of a compound corresponding to formula (III) wherein $R^3$ is ethyl from diethyl 2-methylterepthtalate.

One aspect of the invention provides a new method for the preparation of 5-cyanophthalide without the need for 5-carboxyphthalide.

DETAILED DESCRIPTION OF THE INVENTION

As indicated above the inventors have simplified the known process for the production of 5-cyanophthalide which is an intermediate in the manufacturing of the medicaments citalopram and escitalopram. Instead of producing 5-carboxyphthalide as done previously, the inventors have now provided a method for the manufacturing of alkoxycarbonylphtalides which are very suitable for the downstream production of citalopram/escitalopram and their intermediates. The developed method is suitable for large scale production and the alkoxycarbonylphtalides are obtained in high purity and in high yields. In further aspects, the inventors have provided improved manufacturing conditions for the production of intermediates suitable for the manufacturing of citalopram or escitalopram. In preferred embodiments of the invention, alkoxycarbonylphtalides are provided as disclosed herein with improved filtration properties, in particular as compared to 5-carboxyphthalide. In further embodiments, alkoxycarbonylphtalides are provided as disclosed herein with improved solubility properties, in particular as compared to 5-carboxyphthalide.

Accordingly, the present invention provides a method for preparing an alkoxycarbonylphtalide of formula (III)

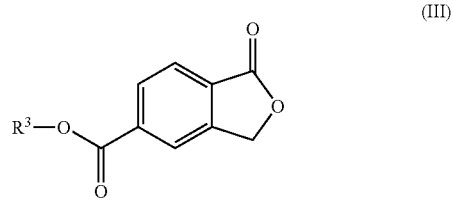

(III)

comprising:
(a) reacting a compound of formula (VIII) with a formaldehyde and oleum; and

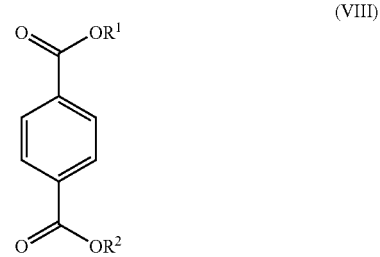

(VIII)

(b) addition of an alcohol $R^3$—OH to the reaction of step (a), thus quenching the reaction with an alcohol;
wherein $R^1$ and $R^2$ is selected independently from H and a $C_{1-6}$-alkyl; and
wherein $R^3$ is a $C_{1-6}$-alkyl or phenyl.

The term $C_{1-6}$ alkyl as used herein refers to a branched or unbranched alkyl group having from one to six carbon atoms inclusive, including but not limited to methyl, ethyl, n-propyl, iso-propyl, n-butyl, iso-butyl, sec.-butyl, tert-butyl, n-pentyl, isopentyl, neopentyl, isohexyl, and n-hexyl. The prefix n indicates that the carbons form a continuous chain with no branching. As described above $R^3$ is a $C_{1-6}$-alkyl or phenyl. Thus, within the invention is embodiments where $R^3$ is ethyl or n-butyl; or where $R^3$ is a $C_4$-alkyl, preferably n-butyl. In further aspect of the invention, $R^3$ is not methyl; not ethyl; or not methyl nor ethyl. In preferred embodiments of the invention $R^3$ is a $C_{3-6}$-alkyl; or $R^3$ is a $C_{4-6}$-alkyl as described above. The $C_{4-6}$alkyl can, e.g., be selected from the group consisting of n-butyl, isopentyl, n-pentyl, neopentyl, isohexyl, 3 methylpentyl, n-hexyl, and preferably n-butyl.

As indicated above $R^1$ and $R^2$ are selected independently from H and a $C_{1-6}$-alkyl. In a preferred embodiment $R^1$ and $R^2$ are selected independently from the group consisting of hydrogen, methyl, ethyl and n-butyl. In further embodiments $R^1$ is different from $R^2$. In one embodiment, not both $R^1$ and $R^2$ is H, i.e. within the invention $R^1$ and $R^2$ is as described herein with the proviso that not both $R^1$ and $R^2$ is H. In preferred embodiments $R^1$ is identical to $R^2$, e.g. where $R^1$ and $R^2$ are identically methyl, ethyl, n-propyl, iso-propyl, n-butyl, iso-butyl, sec.-butyl, tert-butyl, n-pentyl or n-hexyl, preferably $R^1$ and $R^2$ are identically methyl, ethyl or n-butyl. In other embodiments of the invention $R^1$ and $R^2$ are H.

Further examples of embodiments are: $R^1$ and $R^2$ are identically methyl or n-butyl and $R^3$ is ethyl or n-butyl; $R^1$ and $R^2$ are identically methyl or n-butyl and $R^3$ is ethyl; $R^1$ and $R^2$ are identically methyl or n-butyl and $R^3$ is n-butyl; $R^1$ and $R^2$ are methyl and $R^3$ is ethyl or n-butyl; $R^1$ and $R^2$ are n-butyl and $R^3$ is ethyl or n-butyl; $R^1$ and $R^2$ are methyl and $R^3$ is ethyl; $R^1$ and $R^2$ are n-butyl and $R^3$ is ethyl; or $R^1$ and $R^2$ are n-butyl and $R^3$ is n-butyl;

$R^1$ and $R^2$ are H, and $R^3$ is not methyl nor ethyl;
$R^1$ and $R^2$ are H and $R^3$ is a $C_{3-6}$-alkyl or a $C_{4-6}$-alkyl, preferably a $C_4$-alkyl, preferably n-butyl;
$R^1$ and $R^2$ are methyl and $R^3$ is a $C_{3-6}$-alkyl or a $C_{4-6}$-alkyl, preferably $R^3$ is a $C_4$-alkyl, preferably n-butyl; and
$R^1$ and $R^2$ are ethyl and $R^3$ is a $C_{3-6}$-alkyl or a $C_{4-6}$-alkyl, preferably $R^3$ is a $C_4$-alkyl, preferably n-butyl.

The term "formaldehyde" designates as used throughout the description and claims formaldehyde of the formula $CH_2O$ as well as oligomers and polymers thereof. The formaldehyde may be gaseous, however liquid or solid forms are preferred, e.g. paraformaldehyde, trioxane or tri(oxymethylene). In a preferred embodiment the formaldehyde is used in one of its solid forms, e.g. in form of its precursor 1,3,5-trioxane of formula (IX) or paraformaldehyde.

(IX)

Preferably in step (a) is used 1-3 equivalents, such as 1-2.5; 1-2; or 1-1.5 equivalents of the formaldehyde per equivalent of the compound of formula (VIII).

The compound of formula (VIII) may be purchased from commercial sources or it may be prepared by any suitable methods known by the person skilled in the art, cf. e.g. J. Chem. Soc.; 77; 1900; 278. For example terephthalic acid—i.e. formula (VIII), wherein $R^1$ and $R^2$ are H—is commercial available and can be prepared by several known methods, such as by catalytic oxidation of p-xylene. Terephthalic acid can be converted into esters of formula (VIII) wherein $R^1$ and $R^2$ are independently selected from $C_{1-6}$-alkyl by methods known to those skilled in the art.

In a broad aspect, the invention relates to use of a compound of formula (VIIIa) in all the methods of the invention as disclosed herein such that the compound of formula (VIIIa) replaces the compound of formula VIII.

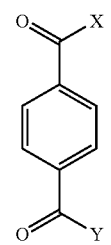

(VIIIa)

X and Y of formula (VIIIa) may be selected independently from the group consisting of: OH, a $C_{1-6}$-alkoxy, a halogen (such as Cl, Br, I), and NR; wherein R is H or a $C_{1-6}$-alkyl. It is understood that the $C_{1-6}$-alkyl part of the $C_{1-6}$-alkoxy in this context may be as indicated herein for $R^1$ and $R^2$ in formula (VIII). Evidently, when X and Y is selected independently from OH and a $C_{1-6}$-alkoxy then formula (VIIIa) is identical to formula (VII) as described herein.

Accordingly, it is within the scope of invention to use terephthaloyl dichloride (formula B) instead of the compound of formula (VIII) in any of the processes of the invention as described herein. Terephthaloyl dichloride is commercial available.

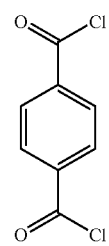

(B)

Those skilled in the art will know how to manufacture compounds of formula (VIII) wherein $R^1$ and $R^2$ are $C_{1-6}$ alkyl form e.g. terephthalic acid or terephthaloyl dichloride by conventional methods.

The inventors have found that terephthaloyl dihalides, especially terephthaloyl dichloride have a better solubility in oleum than terephthalic acid. Additionally, the reaction mixture derived from this starting material, i.e. during step (a) as disclosed herein, has good properties for production at industrial scale. For example the foam is considerably reduced when using terephthaloyl dichloride as starting material as compared to a similar process using terephthalic acid. Also when using terephthaloyl dichloride as starting material the reaction mixture of step (a) may be cooled down to room temparture before the addition of the alcohol, whereas usually this step is performed at higher temperatures when using terephthalic acid as starting material.

Accordingly, in further embodiments, the reaction mixture of step (a) is cooled down to a temperature of less than 40° C., such as less than 35° C., less than 30° C., e.g. in the range 15-30° C., such as 18-30° C. or 18-25° C., preferably at room temperature, before the addition of the alcohol.

Accordingly, within the invention is a method as described herein, in which step (b) is performed at temperatures less than 40° C., such as less than 35° C., less than 30° C., e.g. in the range 15-30° C., such as about 18-30° C. or 18-25° C., preferably at room temperature.

Oleum is also named fuming sulfuring acid, i.e. sulfuric acid containing $SO_3$. The oleum used may be commercially available oleum, e.g. the following are available from Aldrich/Fluka: 12-17% $SO_3$ (Fuming sulfuric acid)=15% oleum; 18-24% $SO_3$ (Fuming sulfuric acid)=20% oleum; 27-33% $SO_3$ (Fuming sulfuric acid)=30% oleum.

In preferred embodiments of the invention, the oleum contains at least 15% $SO_3$, e.g. in the range of 15-65% $SO_3$; such as 12-17% $SO_3$; 16-18% $SO_3$, e.g. below 20%, but preferably higher than 14%. In further embodiments it is preferred that the oleum contains at least 20% $SO_3$, e.g. in the range of 20-40%; 22-33% or 25-30%. The percentages is meant to indicate the $SO_3$ content as present, i.e. e.g. 15% oleum in the "12-17%" $SO_3$ (Fuming sulfuric acid) described above.

Accordingly, in a preferred embodiment, in step (a) is used an oleum as described herein in amounts of 1-8 l per kg of formula (VIII), such as 1.5-6 l/Kg; 1.5-4 l/Kg; 1.5-3.5 l/kg, preferably in the range of 1.5-3.5 l/kg. Preferably, in step (a) 1-2.5, such as 1-2 or 1.25-1.75, equivalents $SO_3$ per equivalent of the compound of formula (VIII) are used.

Preferably no filtration step is performed between step (a) and (b). Accordingly, within the invention are also embodiments as described herein where the product mixture of step (a) is not subjected to an isolation procedure before the addition of the alcohol in step (b). Furthermore, in one embodiment, the reaction in step (a) and/or (b) is not performed in a sealed container, in particular not in a sealed glass tube.

The reaction in step (a) is preferably performed at elevated temperatures, e.g. at a temperature in the range of 115° C.-175° C.; 120° C.-165° C.; 115° C.-150° C.; 115° C.-145° C., preferably 120° C.-140° C. In further embodiments of the invention, step (a) is performed at a relatively high temperature, preferably at a temperature from about 145° C., e.g. in the range of 150° C.-175° C., such as 150° C.-160° C. Within the invention is also embodiments where in step (a) a solution of the compound of formula (VIII) in oleum is heated to a temperature as described above before the addition of the formaldehyde, preferably paraformaldehyde in oleum, cf. Example 6.

When using an oleum having a lower $SO_3$ content, e.g. less than 20% $SO_3$ (e.g. in the range of 16-19% $SO_3$ or 16-18% $SO_3$), the temperature in step (a) is conveniently relatively high, such as at a temperature from about 145° C., e.g. in the range of 150° C.-175° C., such as 150° C.-160° C. When using an oleum having a relatively high $SO_3$ content, e.g. at and above 20% $SO_3$ (e.g. in the range of in the range of 20-40%; 22-33% or 25-30% $SO_3$) the temperature in step (a) is conveniently relatively lower, such as at a temperature in the range of 115° C.-145° C.; 120° C.-145° C.; or 120° C.-140° C.

The duration of the reaction in step (a), i.e. before the addition of the alcohol in step (b) should be sufficient to allow the desired reaction to proceed. Preferably, the reaction in step (a) is performed for at least 1 hour, preferably in the range of 1-24 hours, e.g. 2-18 hours, 2-10 hours, and preferably 2-5 hours.

Step (b) is preferably performed at a temperature below the boiling point of the alcohol. When the alcohol used for quenching is n-butanol, then during step (b) the temperature is preferably in the range of 60-110° C., such as 70-110° C. preferably in the range of 75° C.-100° C., or 75° C.-85° C.

After quenching the reaction in step (b) with an alcohol, the reaction is preferably cooled down to a lower temperature to assist the crystallization, e.g. down to a temperature less than 40° C.

Preferably the alkoxycarbonylphtalide of step (b) is subjected to isolation procedures, preferably to obtain an essentially isolated product. The alkoxycarbonylphtalide may be isolated by filtration, or in alternative by decanting. Thus, preferably, the method of the invention comprises collecting the alkoxycarbonylphtalide by filtration. The alkoxycarbonylphtalide produced in a process of the invention may also be further purified by washing, e.g. in alcohol and/or water followed by additional filtration to collect the product. In further embodiments, the method of the invention comprises purification of the alkoxycarbonylphtalide by addition of an organic solvent (e.g. toluene, optionally in combination with a higher alkane, such as heptane) and aqueous solvent (preferably water) thereby extracting the alkoxycarbonylphtalide into the organic phase, preferably followed by collecting the extracted alkoxycarbonylphtalide by filtration. Accordingly, in further embodiments the method of the invention comprises purifying the alkoxycarbonylphtalide, e.g. butoxycarbonylphtalide, by dissolution in a mixture of toluene and heptanes; precipitation by cooling; filtration, and then drying the resulting product. The method of the invention may also comprise a step of addition of NaOH to a pH of about 4 to remove unreacted phthalic acid followed by filtration. Further purification may, if desired, be performed by recrystallisation, e.g. in a mixture of toluene and heptanes or in methanol.

Diphthalide (Formula A) impurities may be formed by this type of reaction starting from the compound of formula (VIII).

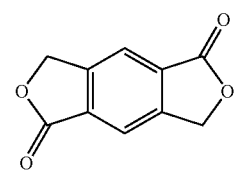

(A)

The diphthalide impurity is preferably removed. This is advantageously done by dissolving the crude alkoxycarbonylphtalide, e.g. butoxycarbonylphtalide, product in a mixture of toluene and heptanes (e.g. two volumes of toluene and two of heptanes per amount of crude butoxycarbonylphtalide); heating the mixture to 80° C.; treating with activated carbon and a filter aid, such as dicalite, and performing a pressure filtration at this temperature; cooling the resulting mixture to 25° C. over a period of 5 hours; keep at 25° C. for 2 hours before the purified product is filtered off. The described purification method is able to reduce the diphthalide level in the crude product from over 5% to less than 0.3% in the purified product. One further advantage of preparing a carboalkoxyphtahlide of formula (III) instead of 5-carboxyphthalide for the subsequent production of citalopram /escitalopram is that the product purified with respect to diphthalide impurities is precipitated from an organic solvent which make it easier to dry than the 5-carboxyphthalide product obtained from aqueous solution when removing diphthalide impurities from crude 5-carboxyphthalide.

It is further preferred that the alkoxycarbonylphtalide produced by a method of the invention is dried, i.e. subjected to a drying procedure lowering the liquid content, i.e. of the precipitate preferably collected by filtration. The product prepared by a process of the invention is preferably in the form of powder which expression refer to a collection of essentially dry particles, i.e. the moisture content being below about 10% by weight, preferably below 8% by weight, such as below 6% by weight, 4% by weight.

Preferably, the alkoxycarbonylphtalide product produced by a method of the invention as described herein has a purity of at least 20%, preferably at least 50%, e.g. at least 75%, at least 85%, or at least 90% as measured by HPLC. The alkoxycarbonylphtalide product produced by a method of the invention preferably has a purity of less than 99%, or less than 98%, less than 95%, such as less than 90% pure as measured by HPLC. In other embodiments, the alkoxycarbonylphtalide product prepared by a method of the invention has a purity between 80-99%, such as 90-98%, e.g. 95-98% or 80-95%.

The alkoxycarbonylphtalide product of the invention is conveniently used for the production of 5-cyanophthalide. Thus, the alkoxycarbonylphtalide product of the invention may be converted to the amid of formula (IV), wherein R is H or $C_{1-6}$-alkyl, by amidation with ammonia or a $C_{1-6}$-alkylamine, e.g., t-butyl amine.

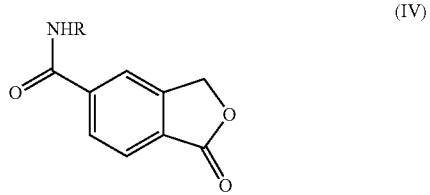

(IV)

The amide of Formula (IV) may then be reacted with a dehydrating agent, e.g. $SOCl_2$, to obtain the 5-cyanophthalide.

Accordingly, the present invention also relates to methods for the synthesis of 5-cyanophthalide starting from a alkoxycarbonylphtalide prepared by a method of the invention, i.e. in particular within the scope of the invention are embodiments where $R^1$, $R^2$ and $R^3$ are as defined above. Thus, in particularly preferred embodiments $R^3$ is a $C_{3-6}$-alkyl; $R^3$ is a $C_{4-6}$-alkyl; or is $R^3$ is a $C_4$-alkyl, preferably n-butyl. Likewise, within the scope of the invention is also a method for the preparation of 5-cyanophthalide comprising a method as described herein for preparing an alkoxycarbonylphtalide of formula (III). Within the scope of the invention are also methods for the synthesis of citalopram or escitalopram comprising a method of the invention for the synthesis of 5-cyanophthalide. As indicated above it is of significant value that the present invention provides a process for preparing intermediates like 5-cyanophtahlide comprising one step less as compared to the known process of preparing 5-cyanophtahlide through 5-carboxyphthlide.

Accordingly, in further aspects, the invention relates to a method for the synthesis of citalopram or escitalopram from the alkoxycarbonylphtalide of formula (III) as defined herein, in particular where the alkoxycarbonylphtalide has been prepared by a method as disclosed herein, i.e. within the scope of the invention is embodiments where $R^1$, $R^2$ and $R^3$ are as defined herein. In particularly preferred embodiment, $R^3$ is a $C_{3-6}$-alkyl; $R^3$ is a $C_{4-6}$-alkyl; or is $R^3$ is a $C_4$-alkyl, preferably n-butyl.

As mentioned above citalopram is the racemate, whereas escitalopram is the S-enantiomer form essentially without the R-enatiomer form. Escitalopram, may be prepared by the method described in U.S. Pat. No. 4,943,590, i.e. by separating the enantiomers of the intermediate of Formula (II) and performing enantioselective ring closure in order to obtain the desired enantiomer.

In a broad aspect the invention relates to use of a method as disclosed herein for the preparation of a medicament, such as but not limited to, citalopram or escitalopram.

The inventors have found that dialkyl terephthalate, such as dimethyl-, and diethyl terephthalate and terephthaloyl dihalides such as terephthaloyl dichloride (formula B) is more soluble in oleum than terephthalic acid. Thus, in a preferred embodiment, $R^1$ and $R^2$ of formula (VIII) is not hydrogen; likewise X and Y of formula (VIIIa) are not OH.

The inventors have also found that the n-butyl ester of formula m (i.e. $R_3$=n-butyl) has better filtration properties and is more soluble than 5-carboxyphthalide. Accordingly, in a preferred embodiment, an ester having one or more of such characteristics are used as starting material for the production of citalopram or escitalopram, advantageously trough the intermediate 5-cyanophthalide as described herein. Thus, in one aspect, the invention relates to a method for preparing an intermediate suitable for the synthesis of citalopram or escitalopram, said method comprising the steps of:

(i) preparing a alkoxycarbonylphtalide of formula (III),

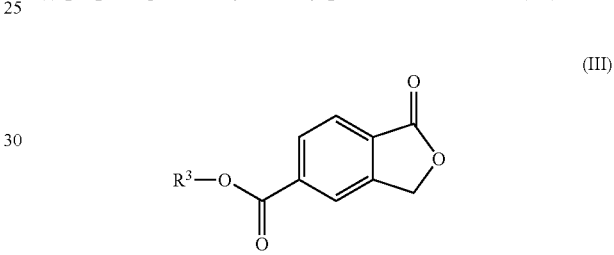

(III)

wherein $R^3$ is a $C_{1-6}$-alkyl as defined herein, e.g. a $C_{3-6}$-alkyl or a $C_{4-6}$-alkyl, such as a $C_4$-alkyl, preferably n-butyl.

(ii) subjecting the alkoxycarbonylphtalide of formula (III) to an isolation procedure, said isolation procedure preferably comprising a filtration step.

The alkoxycarbonylphtalide in step (i) may be prepared by any of the methods described herein, i.e. with step (a) and (b); or, e.g., by a method comprising the step of:

(c) esterification of 5-carboxyphthalide of formula (VI).

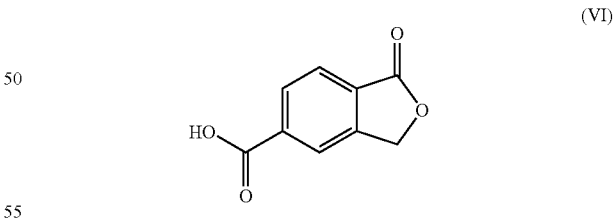

(VI)

The 5-carboxyphthalide may be obtained by the methods described in U.S. Pat. Nos. 3,607,884; 6,403,813; 6,458,973; DE 2630927; or Forney, L. S, J. Org. Chem. 1970, 35, p. 1695-1696. Preferably, the 5-carboxyphthalide in step (c) is prepared by a method comprising: (d) reacting the compound of formula (VIII), wherein $R^1$ and $R^2$ are as defined herein, with a formaldehyde and oleum; and (e) addition of an aqueous solution, preferably water. Thus, $R^1$ and $R^2$ are preferably selected independently from H and a $C_{1-6}$-alkyl. As indicated above, in a preferred embodiment $R^1$ and $R^2$ is selected independently from the group consisting of hydrogen, methyl, ethyl and n-butyl. In further embodiments $R^1$ is different from $R^2$. In one embodiment, at least one of $R^1$ and $R^2$ is not H. Also within the invention is embodiments wherein $R^1$ is identical to $R^2$, e.g. where $R^1$ and $R^2$ are identically methyl, ethyl, n-propyl, iso-propyl, n-butyl, iso-butyl, sec.-butyl, tert-butyl, n-pentyl or n-hexyl, preferably $R^1$ and $R^2$ are identically methyl, ethyl or n-butyl. In other embodiments of the invention, $R^1$ and $R^2$ are H. As indicated above within the scope of the invention is also methods as described herein where the compound of formula (B) is used instead of the compound of formula (VIII).

Preferably the 5-carboxyphthalide is not dried, i.e. subjected to a drying procedure such as oven or drying on a filter nutche before the esterification in step (c). In a preferred embodiment, the prepared 5-carboxyphthalide is not isolated, e.g. by filtration, before the esterification in step c). In a preferred embodiment, the 5-carboxyphthalide is converted to the corresponding ester in step c) after azeotropic drying, e.g. with toluene or another organic solvent providing similar effect.

The esterification in step (c) may be obtained:
(i) by treatment of 5-carboxyphthalide with an alcohol $R^3$—OH in the presence of an acid, wherein $R^3$ is as defined herein, preferably a mineral acid or a Lewis acid, such as HCl, $H_2SO_4$, $POCl_3$, $PCl_5$ or $SOCl_2$; or
(ii) (ii) from the corresponding acid chloride of formula (X) by reaction with an alcohol $R^3$—OH, wherein $R^3$ is as defined herein for formula (III), preferably said acid chloride is prepared by treatment of 5-carboxyphthalide with $POCl_3$, $PCl_5$ or $SOCl_2$ neat or in a suitable solvent, such as toluene or toluene comprising a catalytic amount of N,N-dimethylformamide.

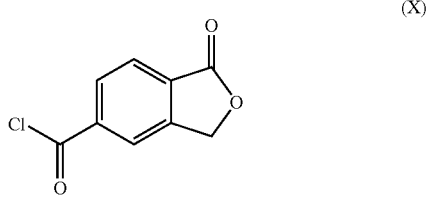

It is understood that the term "intermediate" as used in the context of "method for preparing an intermediate suitable for the synthesis of citalopram or escitalopram" includes 5-cyanophthalide and also the alkoxycarbonylphtalide as such. Thus, the alkoxycarbonylphtalide may be subjected to further process steps, e.g. as disclosed herein for the synthesis of 5-cyanophthalide and finally to citalopram and escitalopram.

It is understood that the above mentioned method for preparing an intermediate suitable for the synthesis of citalopram or escitalopram may be subjected to any of the corresponding process condition as indicated above for the method of the invention for preparing a alkoxycarbonylphtalide, in particular with respect to further purification procedures, such as by washing, recrystallisation, additional filtration and drying of the alkoxycarbonylphtalide product. Additionally, the above mentioned preferred properties for the alkoxycarbonylphtalide likewise applies to the alkoxycarbonylphtalide produced in the present context by the process of the invention comprising steps (i) and (ii), e.g. the indicated moisture contents and purities.

In its broad aspect, the invention relates to alkoxycarbonylphtalide of formula (III),

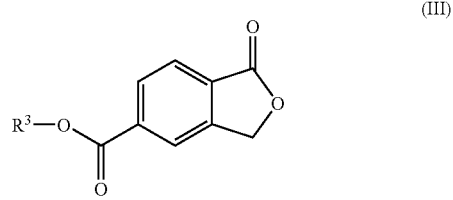

wherein $R^3$ is a $C_1$-$C_6$-alkyl or phenyl, as described herein. Accordingly, the invention also relates to a alkoxycarbonylphtalide product obtainable or obtained by any of the methods of the invention as described herein.

Within the invention is also a method for preparing 5-carboxyphthalide which method comprises the steps of: (i) reacting terephthalic acid with a formaldehyde, preferably paraformaldehyde, and oleum at a temperature in the range of 150° C.-175° C., preferably at a temperature in the range of 150° C.-160° C.; (ii) addition of an aqueous solution, preferably water; and (iii) one or more isolation procedures, e.g. filtration. In further embodiments, the type of formaldehyde, e.g. paraformaldehyde, the amounts used, the time intervals, etc. may be as disclosed herein for the method of the invention for preparing a alkoxycarbonylphtalide of formula (III), i.e. with the appropriate modifications to the present method for preparing 5-carboxyphthalide. Preferably, the reaction mixture of step (i) is cooled to a temperature below the boiling point of water before performing step (ii). This aspect of the invention is further illustrated by Example 6.

The diphthalide impurity (Formula A) is preferably removed from carboxyphtalide by the following procedure. Crude carboxyphtalide is suspended in water (e.g. five volumes) and pH is adjusted to 9 by addition of triethylamine. Alternatively the suspension is adjusted with sodium hydroxide to approx. pH 6 and then with triethylamine to pH 9. Filter aid is added and the suspension is filtered. After acidification the purified product is isolated. The described method is able to reduce the diphthalide level from over 10% to below 0.2% in the purified product. Another advantage of the described method is the increased productivity due to the much lower total volume required when using triethylamine instead of sodium hydroxide for the pH adjustment.

The invention is further illustrated by the following examples which, however, are not to be construed as limiting the scope of protection.

EXAMPLES

Example 1

5-Ethoxycarbonylphtalide

Oleum (20-25% $SO_3$, 800 g), dimethyl terephthalate (234 g) and paraformaldehyde (48 g) are heated with stirring for 5 hours at 125° C. The reaction mixture is cooled to 70° C. and poured into ethanol (1,6 L) having room temperature. This mixture is heated to reflux for 1½ hour before ice (800 g) is added. The suspension is stirred overnight, filtered off and washed with ethanol (150 ml). The crude product is suspended in water (800 ml) and pH is adjusted to 4 with NaOH (27%). The precipitate is filtered off and washed with water and dried.

Yield: 192 g

Molar yield: 66.9% (corrected for purity based on HPLC area %)

As used herein the theoretical yield in an organic reaction is the weight of product which would be obtained if the reaction had proceeded to completion according to the chemical equation. The yield is the weight of the pure product, which is isolated from the reaction. The percentage yield may be expressed thus:

$$\text{Yield (\%)} = \frac{\text{weight of product}}{\text{theoretical yield}} \times 100 \times \text{purity based on } HPLC \text{ area (\%)}$$

Example 2

5-Ethoxycarbonylphtalide Large Scale

Oleum (20-25% $SO_3$, 160 L) is charged into a glass reactor (400 L) and under stirring dimethyl terephthalate (90.7 kg) is added to the reactor. Paraformaldehyde (18.6 kg) is added and the reaction mixture is agitated at 125° C. for 5 hours. The reaction mixture is cooled to 70° C. and added to a reactor containing ethanol (620 L) which has ambient temperature about 20° C. The mixture is heated at 85-93° C. for 1½ hour and then cooled to approximated 80° C. before ice (240 kg) is added. After stirring overnight the mixture is cooled to 15° C. and the precipitate is filtered off and washed with water (150 L). The crude 5-ethoxycarbonylphtalide is added to a stirred mixture of water (250 L) to this slurry is added NaOH (27.7%, approximated 250 L) to a pH about 4. The precipitate is filtered off and washed with water (500 L) and dried.

Yield: 83%.

Example 3

5-Butoxycarbonylphtalide

Oleum (25% $SO_3$, 95 ml) is charged into a reactor (350 ml). Under stirring terephthalic acid (19.0 g; 0.11 mol) is added to the reactor and the mixture is heated to 60° C. After stirring for additional 30 min terephthalic acid (31.0 g; 0.19 mol) is added and the mixture is heated to 100° C. for 1 hour. The mixture is cooled to 25-30° C., trioxane (12.0 g; 0.13 mol) is added in portions and the reaction mixture is heated slowly to 130-135° C. and agitated at this temperature for 1½ hours and for 4 hours at 155° C. The reaction mixture is cooled to 40° C. and added to a reactor containing butanol (150 ml) and heptanes (150 ml) witch has been heated to 95-100° C. The formed precipitates were diluted with butanol (85 ml) and stirring overnight. The precipitate is filtered off and dried.

Yield: 47.0 g

Molar yield: 53.6% (corrected for purity based on HPLC area %)

Example 4

5Butoxycarbonylphtalide

Oleum (25% $SO_3$, 95 ml) is charged into a reactor (350 ml). Under stirring terephthalic acid (19.0 g; 0.11 mol) is added to the reactor and the mixture is heated to 60° C. After stirring for additional 30 min terephthalic acid (31.0 g; 0.19 mol) is added and the mixture is heated to 100° C. for 1 hour. The mixture is cooled to 25-30°C., trioxane (12.0 g; 0.13 mol) is added in portions and the reaction mixture is heated slowly to 130-135°C. and agitated at this temperature for 1½ hours and for 4 hours at 155° C. The reaction mixture is cooled to 40° C. and over a period of 30 min added to a reactor containing butanol (300 ml) which has been heated to 95-100° C. Toluene (100 ml) and water (100 ml) was added to the formed suspension. The organic phase was separated and concentrated to dryness and redissolved in toluene (100 ml) and heptanes (100 ml) by heating at 75-80° C. The mixture was cooled to 25-30°C. for 30 min and the product was filtered off and dried.

Yield: 33.8 g,

Molar yield: 44.3% (corrected for purity based on HPLC area %)

Example 5

5-Butoxycarbonylphtalide

Oleum (25% $SO_3$, 95 ml) is charged into a reactor (350 ml). Under stirring terephthalic acid (19.0 g; 0.11 mol) is added to the reactor and the mixture is heated to 60° C. After stirring for additional 40 min terephthalic acid (31.0 g; 0.19 mol) is added and the mixture is heated to 100° C. for 1 hour. The mixture is cooled to 25-30° C., trioxane (12.0 g; 0.13 mol) is added in portions and the reaction mixture is heated slowly to 120-125° C. and agitated at this temperature for 2 hours and for 4 hours at 145° C. The reaction mixture is cooled to 70° C. and added to a reactor containing butanol (350 ml) which has been heated to 65-70° C. over period of 45 min. The formed precipitates were diluted with butanol (150 ml) and stirring overnight at 40° C. The mixture was heated to reflux for 3 hours, cooled to 50-55° C. and water (500 ml) and heptane (500 ml) were added. The product was filtered off and dried.

Yield: 35.4 g,

Molar yield: 44.2% (corrected for purity based on HPLC area %)

Example 6

5-Carboxyphthalide—"High Temperature"

A solution of terephthalic acid (30 g) in oleum (20-25% $SO_3$, 70 ml) is heated to 150° C. To this solution is added a solution of paraformaldehyde (8.8 g) in oleum (20-25% $SO_3$, 37 ml) over a period of 1-2h. The reaction mixture is stirred at 150° C. for additional 4 h and cooled to 90° C. Water (190 ml) is added to the mixture at a rate so that the temperature stays below 100° C. The precipitate is filtered of, washed with hot (90-95° C.) water and suspended in water (200 ml) and dicalite (1.1 g) is added. The pH of the suspension is adjusted to about 7 with NaOH (approximately 60 ml) and activated carbon (1.1 g) is added. The mixture is filtered and the precipitate is rinsed with water. The temperature of the filtrate is adjusted to about 85° C., and the pH is adjusted to about 2 with sulphuric acid (96%, approximated 8 ml). The 5-carboxyphthalide precipitated is separated by filtration and dried.

Yield: 25.7g

Molar yield: 76.4% (corrected for purity based on HPLC area %)

Example 7

Preparing Ester of 5-carboxyphthalide Large Scale 143.7 kg crude wet 5-carboxyphthalide (correspond to app. 39.5 kg dry material) is suspended in toluene (200 L), 1-butanol (42.5 L) and sulfuric acid (3.15 L, 96%). The suspension is heated to reflux (80-85° C.). Water (104,2 kg) removed by a Dean-Stark trap and the end temperature of the reaction mixture is 110° C. The reaction mixture is concentrated by distillation and a total of 85 kg of solvent is removed from the mixture. After cooling to 80° C. heptanes (110 L) is added to the mixture and pH is adjusted to 8 by addition of triethylamine (about 5 L). Activated carbon (1 kg) and Dicalite (1.5 kg) is suspended in heptanes (16 L) and added to the reactor. The temperature is adjusted to 80° C. and pressure filtrated. The filtrate is washed two times with water (2*40 L) and cooled to 25° C. in 5 hours and left at this temperature for 2 hours. The product is filtrated and washed with heptanes (60 L) and dried.

Yield: 43.0 kg

Molar yield: 88.3% (purity based on HPLC area %)

Example 8

5-Butoxycarbonylphtalide from Terephthaloyl Dichloride

Oleum (25% $SO_3$, 50 ml) is charged into a reactor (100 ml). Under stirring terephthaloyl dichloride (25.0g; 0.12 mol) is added to the reactor and the mixture is heated to 80° C. After cooling to 20° C. a mixture of trioxane (44.0 mmol) in dichloromethane (6ml) is added over a period of 30 min. The reaction mixture is heated to 90° C. over a period of 30 min and the dichloromethane is distilled of. The reaction mixture is heated to 140° C. over a period of 1 hour and held at this temperature for 5 hours, cooled to 20° C. and transferred over a period of 2 hours into n-butanol (250ml) that has been heated to 75-80° C. After cooling to 35° C. the formed precipitate was filtered off. The product was washed with a mixture of n-butanol/heptanes 50% and finally with heptanes.

Yield: 14.5g;

Molar yield: 50% (corrected for purity based on HPLC area %)

The invention claimed is:

1. A method for preparing an alkoxycarbonylphtalide of formula (III)

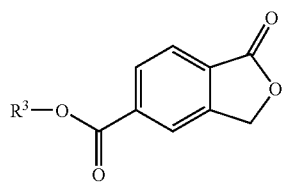

comprising:
(a) reacting a compound of formula (VIIIa) with a formaldehyde and oleum; and

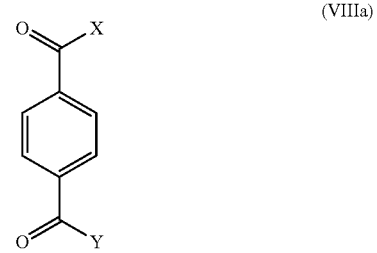

(b) adding the reaction mixture of step (a) to an alcohol of formula R3-OH;
wherein X and Y of formula (VIIIa) are independently selected from: $OR^1$, $OR^2$, a halogen, and $NR_2$;
wherein R, $R^1$ and $R^2$ are independently H or a $C_{1-6}$-alkyl; and $R^3$ is a $C_{1-6}$-alkyl or phenyl.

2. The method according to claim 1 wherein the compound of formula (VIIIa) is a compound of formula (VIII)

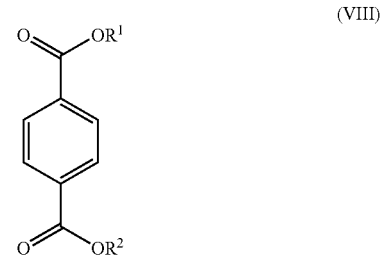

wherein $R^1$ and $R^2$ are selected independently from H and $C_{1-6}$-alkyl.

3. The method of claim 1, wherein the formaldehyde is 1,3,5-trioxane of formula IX

4. The method of claim 1, wherein the formaldehyde is paraformaldehyde.

5. The method of claim 1, wherein $R^1$ and $R^2$ are independently selected from hydrogen, methyl, ethyl, n-propyl, isopropyl, n-butyl, iso-butyl, sec.-butyl, tert-butyl, n-pentyl, and n-hexyl.

6. The method of claim 1, wherein the amount of formaldehyde reacted in step (a) is 1-3 equivalents of the formaldehyde per equivalent of the compound of formula (VIII).

7. The method of claim 1, wherein the amount of oleum reacted in step (a) is 1-8 liters of oleum per kg of formula (VIII).

8. The method of claim 1, wherein the oleum in step (a) contains 18-65% $SO_3$.

9. The method of claim 1, wherein step (a) is performed at a temperature in the range of 115° C.-175° C.

10. The method of claim 1, wherein step (b) is performed at a temperature below the boiling point of the alcohol.

11. The method of claim 1, said method comprising purification of the alkoxycarbonylphtalide by adding an organic solvent and an aqueous solvent to the alkoxycarbonylphtalide, and extracting the alkoxycarbonylphtalide into the organic phase.

12. The method of claim 1, wherein the compound of formula (VIIIa) is terephthaloyl dichloride of formula (B)

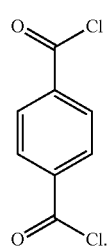

(B)

13. The method of claim 1, comprising converting the alkoxycarbonylphtalide to an amide of formula (IV), wherein $R^4$ is H or $C_{1-6}$-alkyl

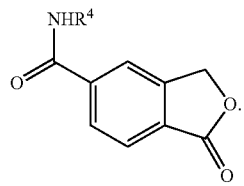

(IV)

14. A method for the synthesis of 5-cyanophthalide comprising the method for preparing an alkoxycarbonylphtalide of formula (III) according to claim 1.

15. A method for the synthesis of citalopram or escitalopram comprising a method for preparing a alkoxycarbonylphtalide of formula (III) according to claim 1.

16. A method for the synthesis of citalopram or escitalopram comprising the method for the synthesis of 5-cyanophthalide according to claim 14.

* * * * *